United States Patent [19]
Purvis et al.

[11] Patent Number: 5,962,038
[45] Date of Patent: Oct. 5, 1999

[54] FRAME FOR HOLDING DENTAL PROSTHESIS PRESS

[75] Inventors: Daniel E. Purvis, Indianapolis, Ind.; Maris J. Lans, Centreville, Va.

[73] Assignee: Eastflex Corp., Indianapolis, Ind.

[21] Appl. No.: 08/903,592

[22] Filed: Jul. 31, 1997

[51] Int. Cl.[6] ..................... B28B 3/00
[52] U.S. Cl. .............. 425/195; 248/121; 249/54; 425/175; 425/451.9; 425/453; 425/179
[58] Field of Search .................. 425/175, 179, 425/451.9, 453, 195; 249/54; 248/121

[56] References Cited

U.S. PATENT DOCUMENTS

| | | | |
|---|---|---|---|
| 162,752 | 5/1875 | Hunt | 425/175 |
| 420,590 | 2/1890 | Davis | 425/175 |
| 663,309 | 12/1900 | Tuttle | 425/175 |
| 3,185,416 | 5/1965 | Osinski | 248/121 |
| 3,267,525 | 8/1966 | McGowan | 249/54 |

*Primary Examiner*—Jan H. Silbaugh
*Assistant Examiner*—Dae Young Lee
*Attorney, Agent, or Firm*—Gipple & Hale

[57] ABSTRACT

A frame is provided for firmly securing a dental press holding one or more flasks during preparation of dental prostheses. The frame securely locks the press in position and facilitates tightening of the press to exert pressure on the dental flasks as well as release of the pressure once the procedure is completed. Use of the frame permits a single technician to tighten and loosen the press with a single hand and allows greater tightening of the press to exclude voids and pockets in the finished prosthesis.

1 Claim, 3 Drawing Sheets

FRAME FOR HOLDING DENTAL PROSTHESIS PRESS

BRIEF DESCRIPTION OF THE INVENTION

The present invention is directed to frame for holding a dental flask and press during compression of the flask and its contents in the manufacture or formation of dentures. More particularly, the present invention relates to a frame which interlocks with a conventional press used for compression of one or more dental flasks, while the dentures are curing so that the press and flasks are rigidly held in proper alignment.

BACKGROUND OF THE INVENTION

In the practice of prosthetic dentistry when preparing dentures the dentist typically prepares an initial trial plate consisting of wax or other similar material in which the prosthetic teeth are set in their proper positions. When this trial denture has been made and fitted to the mouth of the patient and found satisfactory with respect to aesthetics, fit and articulation, it is then subjected to a process in which a permanent plastic material is essentially substituted for the wax. In this process of producing a denture, the trial dentures are attached by wax to a cast which is then placed in one half of a container known as a flask. The two halves of the flask are then secured and plaster is poured into the flask covering the trial denture. When this investment has hardened, the flask containing the investment is heated until the wax is softened enough to be removed. The halves of the investment thereby form a cavity mold already containing the prosthetic teeth in proper position in which a permanent plastic material such as a resin of methyl methacrylate is packed. The halves of the investment are then fitted together and the halves of the flask containing them are forced together in a press. As the two halves of the flask are forced together, excessive plastic material will ooze out between the two opposite faces. Following curing, the flask is removed from the press and excessive plastic material is removed.

Typically the dental flasks which are used in the manufacture or formation of dentures consist of a three part unit having a base, a body and a lid which fit together to comprise an easily removable container for denture molding materials. Various dental flasks together with improvements and variations of these flasks are described, for example, in U.S. Pat. No. 5,338,192 to Weber.

In the actual formation of the dentures, it is necessary that a considerable amount of pressure be applied to the dental flask containing the mold and dental material. This pressure is applied by means of the press into which one or more of the dental flasks are placed. Both the flask and the press must be heavily constructed, typically of bronze. It is necessary that substantial pressure be applied to the flasks which are placed within the press it in order to assure proper alignment of the mold and to force out any air pockets that might result in unwanted porosity. This is achieved by screwing down a plate which compresses onto the flask or flasks. The flask, so compressed is then submerged in hot water for curing.

Heretofore, compression and removal of the dental flasks from their frames has been accomplished by means of a simple hex key and pin. This arrangement has not permitted the dental flask and frame to remain stationary while the press is either compressed or released in order to remove the flasks. Consequently, it has frequently been necessary for more than one technician to actually take part in this procedure. Furthermore, because it requires considerable strength, effort and dexterity to apply the pressure in this way, maximum pressure it not always achieved. It would accordingly be desirable to provide a frame which would firmly and securely hold the dental press both while compression of the dental flasks within the press is taking place and during the procedure whereby the frame is released for removal of the dental flasks. It would especially be desirable if such a frame were to permit the operation of the press in the aforementioned manner by a single technician using only one hand. A further desirable feature would be to provide more complete compression of the frame and dental flasks to thereby eliminate voids or porosity in the final dental prosthesis. These and other desirable objectives are achieved by the present invention.

DETAILED DESCRIPTION OF THE INVENTION

In accordance with the present invention, a frame is provided for holding a dental flask and press for compressing the dental flask or flasks during manufacture or formation of dentures. The frame of the present invention essentially comprises a flat, horizontal base member which engages and holds the base of a dental press between two parallel spaced rails which are mounted on the base member. A vertical support is mounted on the base member of the frame and extends upright from one end of the parallel rails to complete rigid attachment of the press. The upper end of the vertical support member is provided with horizontally extending pin for engaging the upper end of the press in order to hold the press firmly in its upright position while it is either being compressed or released from compression with one or more dental flasks contained within its structure.

Figure 3:
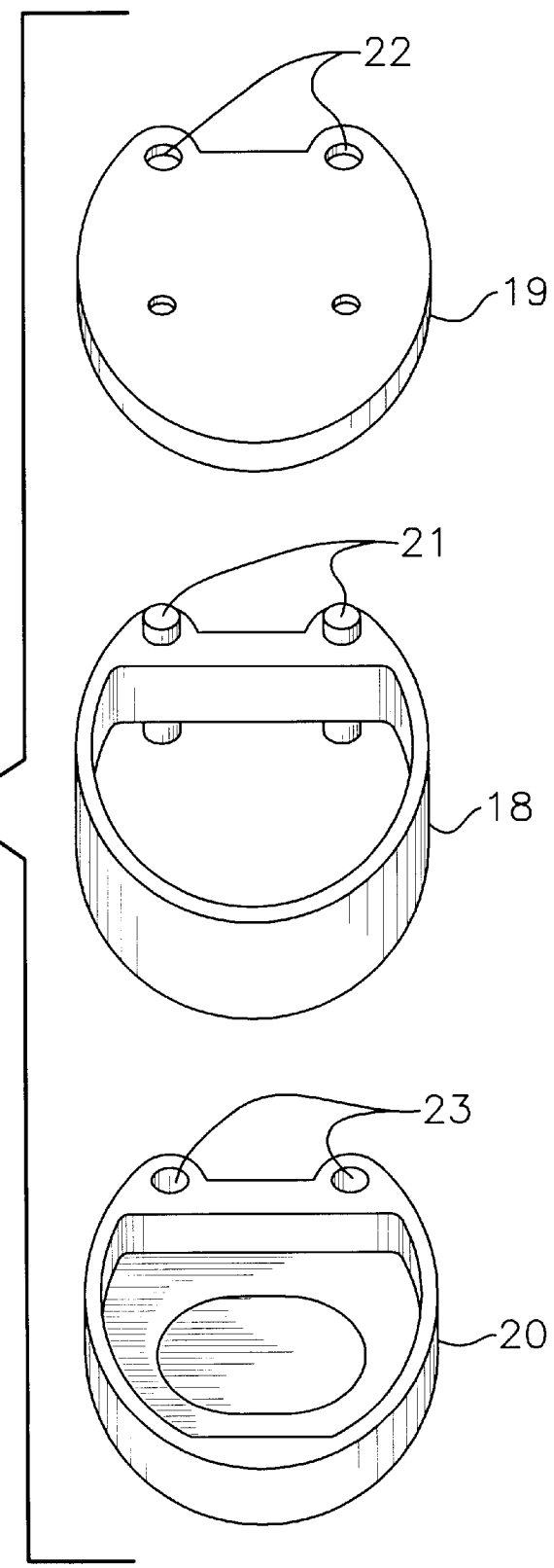
FIG. 3 illustrates in an exploded view the three component parts of a typical dental flask of the prior art.

The present invention will however be more completely understood and appreciated by having reference to the drawings which illustrate both the device of the invention and its use in the manufacture of dentures. Directing attention initially to FIG. 3 of the drawings, a typical dental flask of the prior art is shown consisting of a base 20, body 18 and lid 19. The body of the flask 18 is provided with a pair of pins 21 which engage with holes 22 in lid 19 and holes 23 in base 20 to maintain the closed flask in proper fixed alignment during compression and curing of the dentures.

Figure 1:
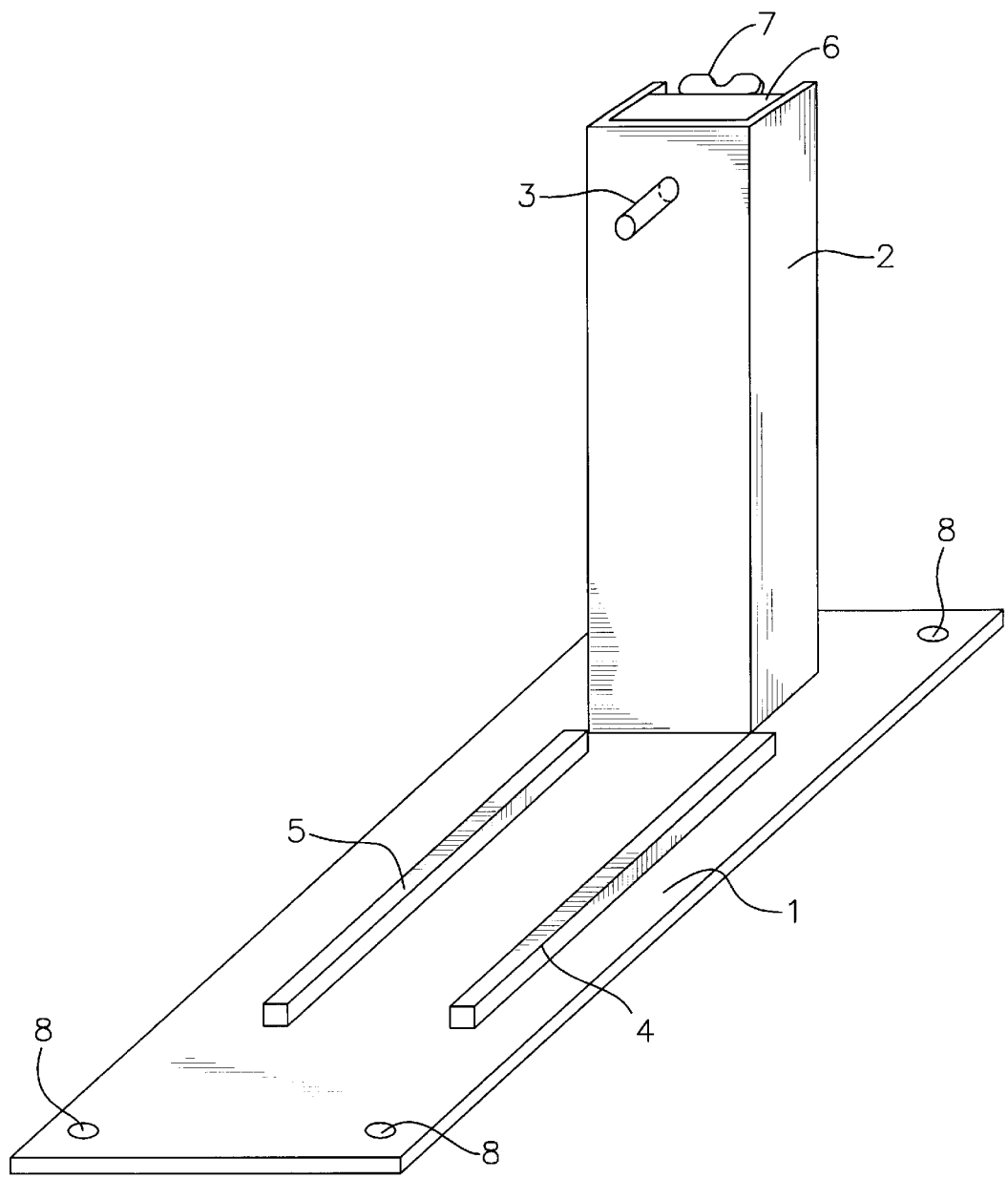
FIG. 1 is a perspective drawing of the dental frame of the present invention.
Figure 2:
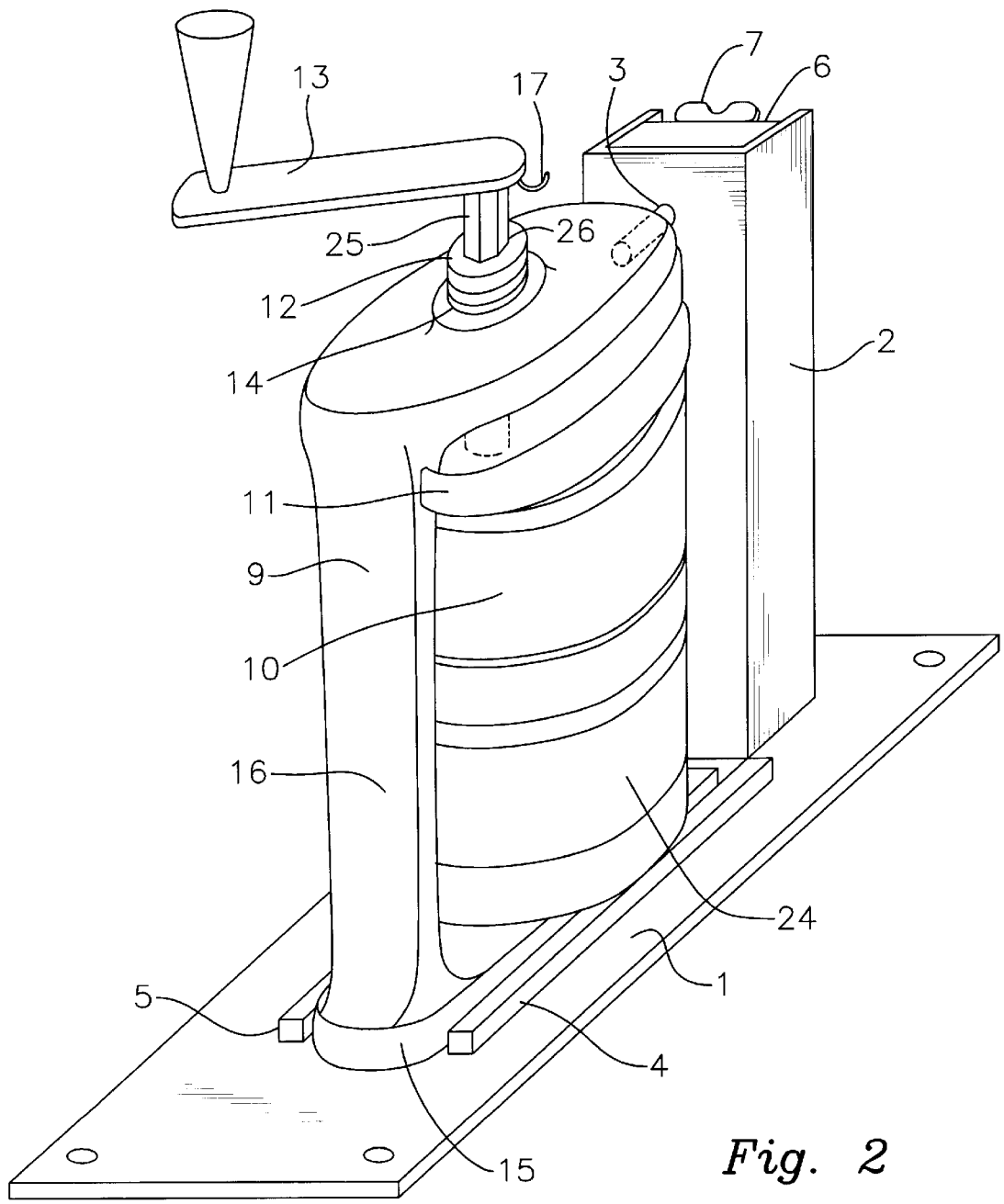
FIG. 2 is perspective drawing illustrating the dental frame of the present invention with a press and dental flasks inserted therein in locked position.

Directing attention next to FIG. 2 of the drawings a dental press 9 typically made of heavy corrosion resistant material such as bronze is shown consisting of flat base 15 having a pair of upright projections 16 on opposite sides of a fixed top plate 14, with a threaded aperture through which a threaded member 12 passes to engage a movable horizontal flat plate 11 which can be retracted or displaced vertically. The threaded member 12 has a hexagonally shaped aperture 26 in its top surface. The pair of dental flasks of the type shown in FIG. 3 of the drawings are shown at 24 and 10 disposed between the base of the press 15 and the top plate 14. A crank 13 is provided which has a hexagonally shaped protrusion 25 extending downwardly to engage the hexagonally shaped aperture 26. By turning crank handle 13, the threaded member 12 is displaced either upward or downward to force moveable plate 11 firmly against the pair of dental flasks disposed beneath it or to retract plate 11 out of contact with the dental flasks to permit their removal. In accordance with the invention, frame 1, which is shown further in FIG. 1 of the drawings, is provided with a pair of horizontal rails 4 and 5 attached to the base of the frame. Base 15 of the press is slidably disposed between the two horizontal rails to lock the press in position against any lateral movement during the turning of crank 13. In order to further secure and stabilize the press, a horizontal pin 3 is disposed on upright support 2 of the frame of the invention and engages within a hole provided and shown in phantom in top plate 14 of the press. Thus, the upper portion of the press is also stabilized by the frame of the invention against any lateral movement during the process of compressing or opening the press.

FIG. 1 of the drawings illustrates the component parts of the frame of the invention. The frame comprises a flat, horizontal plate 1 having horizontal rails 4 and 5 spaced in parallel apart from one another to accommodate the base of a typical dental press as illustrated in FIG. 2 of the drawings. An upright member 2 is attached to base plate 1 of the frame is typically constructed of a "U" shaped member for rigidity and strength. At the upper end of the vertical upright support 2 is horizontal pin 3 which, as previously described, engages within a hole provided in the top plate of the dental press to further stabilize the entire structure. A horizontal cross member is also provided at 6 through which distal end of pin 3 may pass for support and stability. A clip 7 is shown on the upper end of the vertical support to hold the crank 13 when it is not in use. Holes are provided at 8 in the corners of the base plate 1 so that the entire structure can be firmly bolted to a bench or other such surface to stabilize the frame and facilitate operation of the unit by a single individual using only one hand.

Since it is especially necessary that the frame of the invention be rugged and capable of withstanding considerable stress during operation, it is most desirable that the entire unit be constructed of heavy gauge material such as steel although other appropriate metals and materials could as well be employed. It will also be noted in FIG. 2 of the drawings that a hook 17 is provided on crank 13. This hook is used to engage the flask and frames so that they can conveniently be withdrawn from boiling water during the curing procedure. This provides safety and convenience when removing the hot flasks from curing tanks. The handle part of the crank can be made of plastic, wood or any material that insulates the hand from heat. The shape of the handle that attaches the crank will vary as demands dictate.

What is claimed is:

1. A dental device for holding one or more dental flasks during compression or release of the flasks comprising in combination a press for compressing said flasks comprising an elongated base having an upright support member extending from either end thereof said support members terminating at their upper extremity in a single horizontal plate having a threaded through aperture disposed therein for accommodating a threaded elongated member connected at one end to a vertical displaceable horizontal pressure plate, slidably disposed between said support members; said threaded elongated member having a crank handle disposed at its other end for turning said threaded member to cause said vertical displacement of said pressure plate; and a frame for said press comprising a flat, horizontal base member for engaging and holding the base of said press between two parallel, spaced rails mounted on said frame base member, and a vertical support member mounted on said base member and extending upright from one end of said parallel rails, the upper end of said vertical support member being provided with a pin for engaging the horizontal plate of said press to hold said press firmly in upright position while said threaded member is being turned during said compression or release, and being otherwise provided with means for holding said crank and bolt when not disposed in said threaded aperture.

\* \* \* \* \*